United States Patent
Cragg et al.

(10) Patent No.: US 9,358,014 B2
(45) Date of Patent: Jun. 7, 2016

(54) DEVICE AND METHOD FOR CONTROLLING INJECTION OF LIQUID EMBOLIC COMPOSITION

(71) Applicant: Covidien LP, Manfield, MA (US)

(72) Inventors: Andrew H. Cragg, Edina, MD (US); Blair D. Walker, San Clemente, CA (US); John Perl, II, Bratenahl, OH (US); Michael Jones, Capistrano Beach, CA (US); George Robert Greene, Costa Mesa, CA (US); George Wallace, Coto de Caza, CA (US); Richard J. Greff, St. Pete Beach, FL (US)

(73) Assignee: Covidien LP, Mansfield, MA (US)

( * ) Notice: Subject to any disclaimer, the term of this patent is extended or adjusted under 35 U.S.C. 154(b) by 120 days.

(21) Appl. No.: 13/838,947

(22) Filed: Mar. 15, 2013

(65) Prior Publication Data

US 2013/0211443 A1 Aug. 15, 2013

Related U.S. Application Data (63) Continuation of application No. 13/152,208, filed on Jun. 2, 2011, now Pat. No. 8,454,649, which is a continuation of application No. 11/923,495, filed on Oct. 24, 2007, now Pat. No. 7,976,527, which is a (Continued)

(51) Int. Cl.
*A61B 17/12* (2006.01)
*A61B 17/00* (2006.01)
*A61M 25/00* (2006.01)

(52) U.S. Cl.
CPC ....... *A61B 17/12195* (2013.01); *A61B 17/1219* (2013.01); *A61B 17/12022* (2013.01);

(Continued)

(58) Field of Classification Search
CPC .......... A61M 25/0029; A61M 25/003; A61M 25/0067; A61M 25/007; A61M 25/0071; A61M 25/0075; A61M 2025/0004; A61B 17/12181; A61B 17/12186
See application file for complete search history.

(56) References Cited

U.S. PATENT DOCUMENTS 2,326,159 A 8/1943 Mendel
3,058,473 A 10/1962 Whitehead
(Continued)

FOREIGN PATENT DOCUMENTS

DE 1875646 U 7/1963
DE 2541919 3/1977
(Continued)

OTHER PUBLICATIONS

Byrne, J., Review Article: Endovascular Treatments for Intracranial Aneurysms, The British Journal of Radiology, vol. 69, Issue 826, pp. 891-899.

(Continued)

*Primary Examiner* — Laura Bouchelle
(74) *Attorney, Agent, or Firm* — Elizabeth A. O'Brien, Esq.

(57) ABSTRACT

A liquid embolic delivery system is provided for trapping an injected liquid embolic composition to prevent the liquid embolic from solidifying or otherwise passing outside of an embolization area. The delivery system includes a catheter for delivery of a liquid embolic composition and a containment member positioned at a distal end of the catheter which is shaped to trap the liquid embolic composition delivered through the lumen of the catheter. The containment member is formed as a brush, nest, sponge, swab, flexible sack, or other shape into and around which the liquid embolic composition is injected. The liquid embolic composition is trapped or meshes with the containment member during solidification containing the liquid embolic and preventing the embolic composition from passing into the blood stream.

18 Claims, 6 Drawing Sheets

Related U.S. Application Data continuation of application No. 10/242,469, filed on Sep. 13, 2002, now abandoned, which is a continuation of application No. 09/387,274, filed on Aug. 31, 1999, now Pat. No. 6,511,468, which is a continuation-in-part of application No. 08/953,149, filed on Oct. 17, 1997, now Pat. No. 6,146,373.

(52) U.S. Cl.
CPC ..... *A61B17/12113* (2013.01); *A61B 17/12136* (2013.01); *A61B 17/12168* (2013.01); *A61B 17/12172* (2013.01); *A61B 17/12177* (2013.01); *A61B 17/12186* (2013.01); *A61B 17/00491* (2013.01); *A61B 2017/00495* (2013.01); *A61B 2017/00876* (2013.01); *A61B 2017/00893* (2013.01); *A61B 2017/1205* (2013.01); *A61B 2017/12059* (2013.01); *A61B 2017/12063* (2013.01); *A61M 25/00* (2013.01); *A61M 25/0028* (2013.01); *A61M 25/0097* (2013.01); *A61M 2025/004* (2013.01); *A61M 2025/0036* (2013.01)

(56) References Cited

U.S. PATENT DOCUMENTS

| | | |
|---|---|---|
| 3,656,485 A | 4/1972 | Robertson |
| 3,656,486 A | 4/1972 | Robertson |
| 3,674,014 A | 7/1972 | Tillander |
| 3,977,409 A | 8/1976 | Brendling |
| 4,346,712 A | 8/1982 | Handa et al. |
| 4,364,392 A | 12/1982 | Strother et al. |
| 4,385,631 A | 5/1983 | Uthmann |
| 4,395,806 A | 8/1983 | Wonder et al. |
| 4,402,319 A | 9/1983 | Handa et al. |
| 4,468,216 A | 8/1984 | Muto |
| 4,545,367 A | 10/1985 | Tucci |
| 4,631,188 A | 12/1986 | Stoy et al. |
| 4,663,358 A | 5/1987 | Hyon et al. |
| 4,698,056 A | 10/1987 | Ciannella |
| 4,739,768 A | 4/1988 | Engelson |
| 4,808,155 A | 2/1989 | Mahurkar |
| 4,819,637 A | 4/1989 | Dormandy, Jr. |
| 4,863,442 A | 9/1989 | DeMello et al. |
| 4,884,579 A | 12/1989 | Engelson |
| 4,927,642 A | 5/1990 | Kunz |
| 4,932,938 A | 6/1990 | Goldberg et al. |
| 4,936,835 A | 6/1990 | Haaga |
| 5,041,090 A | 8/1991 | Scheglov et al. |
| 5,049,140 A | 9/1991 | Brenner et al. |
| 5,080,655 A | 1/1992 | Haaga |
| 5,084,063 A | 1/1992 | Korthoff |
| 5,092,848 A | 3/1992 | deCiutiis |
| 5,108,407 A | 4/1992 | Geremia et al. |
| 5,122,136 A | 6/1992 | Guglielmi et al. |
| 5,156,596 A | 10/1992 | Balbierz et al. |
| 5,167,622 A | 12/1992 | Muto |
| 5,192,301 A | 3/1993 | Kamiya et al. |
| 5,207,648 A | 5/1993 | Gross |
| 5,215,530 A | 6/1993 | Hogan |
| 5,221,267 A | 6/1993 | Folden |
| 5,258,042 A | 11/1993 | Mehta |
| 5,263,964 A | 11/1993 | Purdy |
| 5,334,217 A | 8/1994 | Das |
| 5,360,414 A | 11/1994 | Yarger |
| 5,360,418 A | 11/1994 | Weilbacher et al. |
| 5,375,612 A | 12/1994 | Cottenceau et al. |
| 5,395,353 A | 3/1995 | Scribner |
| 5,405,339 A | 4/1995 | Kohnen et al. |
| 5,413,791 A | 5/1995 | Rhee et al. |
| 5,443,454 A | 8/1995 | Tanabe et al. |
| 5,569,221 A | 10/1996 | Houser et al. |
| 5,570,585 A | 11/1996 | Vaynberg |
| 5,580,568 A | 12/1996 | Greff et al. |
| 5,603,698 A | 2/1997 | Roberts et al. |
| 5,645,558 A | 7/1997 | Horton |
| 5,667,767 A | 9/1997 | Greff et al. |
| 5,683,370 A | 11/1997 | Luther et al. |
| 5,695,480 A | 12/1997 | Evans et al. |
| 5,702,361 A | 12/1997 | Evans et al. |
| 5,733,267 A | 3/1998 | Del Toro |
| 5,746,734 A | 5/1998 | Dormandy, Jr. et al. |
| 5,749,894 A | 5/1998 | Engelson |
| 5,766,219 A | 6/1998 | Horton |
| 5,776,097 A | 7/1998 | Massoud |
| 5,782,797 A * | 7/1998 | Schweich et al. ............. 604/507 |
| 5,791,036 A | 8/1998 | Goodin et al. |
| 5,795,331 A | 8/1998 | Cragg et al. |
| 5,830,178 A | 11/1998 | Jones et al. |
| 5,833,644 A | 11/1998 | Zadno-Azizi et al. |
| 5,894,022 A | 4/1999 | Ji et al. |
| 5,895,378 A | 4/1999 | Nita |
| 5,895,385 A | 4/1999 | Guglielmi et al. |
| 5,895,410 A | 4/1999 | Forber et al. |
| 5,902,310 A | 5/1999 | Foerster et al. |
| 5,921,954 A | 7/1999 | Mohr, Jr. et al. |
| 5,925,683 A | 7/1999 | Park |
| 5,928,226 A | 7/1999 | Guglielmi et al. |
| 5,928,260 A | 7/1999 | Chin et al. |
| 5,951,599 A | 9/1999 | McCrory |
| 5,957,912 A | 9/1999 | Heitzmann |
| 5,958,444 A | 9/1999 | Wallace et al. |
| 5,984,964 A | 11/1999 | Roberts et al. |
| 6,010,498 A | 1/2000 | Guglielmi |
| 6,015,424 A | 1/2000 | Rosenbluth et al. |
| 6,022,369 A | 2/2000 | Jacobsen et al. |
| 6,044,845 A * | 4/2000 | Lewis ............................ 128/898 |
| 6,051,607 A | 4/2000 | Greff |
| 6,059,815 A | 5/2000 | Lee et al. |
| 6,063,318 A | 5/2000 | Houser et al. |
| 6,077,260 A | 6/2000 | Wheelock et al. |
| 6,090,125 A | 7/2000 | Horton |
| 6,093,199 A | 7/2000 | Brown et al. |
| 6,102,917 A | 8/2000 | Maitland et al. |
| 6,102,932 A | 8/2000 | Kurz |
| 6,136,015 A | 10/2000 | Kurz et al. |
| 6,139,520 A | 10/2000 | McCrory et al. |
| 6,146,373 A | 11/2000 | Cragg et al. |
| 6,152,144 A | 11/2000 | Lesh et al. |
| 6,159,165 A | 12/2000 | Ferrera et al. |
| 6,165,178 A | 12/2000 | Bashiri et al. |
| 6,165,193 A | 12/2000 | Greene, Jr. et al. |
| 6,168,570 B1 | 1/2001 | Ferrera |
| 6,168,615 B1 | 1/2001 | Ken et al. |
| 6,171,326 B1 | 1/2001 | Ferrera et al. |
| 6,179,860 B1 | 1/2001 | Fulton, III et al. |
| 6,203,779 B1 | 3/2001 | Ricci et al. |
| 6,224,610 B1 | 5/2001 | Ferrera |
| 6,228,055 B1 | 5/2001 | Foerster et al. |
| 6,241,691 B1 | 6/2001 | Ferrera et al. |
| 6,245,053 B1 | 6/2001 | Benjamin |
| 6,258,079 B1 | 7/2001 | Burbank et al. |
| 6,265,178 B1 | 7/2001 | Martin, Jr. |
| 6,270,477 B1 | 8/2001 | Bagaoisan et al. |
| 6,277,126 B1 | 8/2001 | Barry et al. |
| 6,293,960 B1 | 9/2001 | Ken |
| 6,296,622 B1 | 10/2001 | Kurz et al. |
| 6,306,153 B1 | 10/2001 | Kurz et al. |
| 6,319,267 B1 | 11/2001 | Kurz |
| 6,346,091 B1 | 2/2002 | Jacobsen et al. |
| 6,361,528 B1 | 3/2002 | Wilson et al. |
| 6,368,301 B1 | 4/2002 | Hamilton et al. |
| 6,375,774 B1 | 4/2002 | Lunn et al. |
| 6,409,721 B1 | 6/2002 | Wheelock et al. |
| 6,463,317 B1 | 10/2002 | Kucharczyk et al. |
| 6,475,169 B2 | 11/2002 | Ferrera |
| 6,478,773 B1 | 11/2002 | Gandhi et al. |
| 6,497,671 B2 | 12/2002 | Ferrera et al. |
| 6,500,190 B2 | 12/2002 | Greene, Jr. et al. |
| 6,511,468 B1 | 1/2003 | Cragg et al. |
| 6,524,274 B1 | 2/2003 | Rosenthal et al. |
| 6,551,340 B1 | 4/2003 | Konya et al. |
| 6,558,367 B1 | 5/2003 | Cragg et al. |
| 6,589,236 B2 | 7/2003 | Wheelock et al. |

(56) References Cited

U.S. PATENT DOCUMENTS

| | | | |
|---|---|---|---|
| 6,596,217 | B1 | 7/2003 | Davis-Lemessy et al. |
| 6,616,617 | B1 | 9/2003 | Ferrera et al. |
| 6,638,291 | B1 | 10/2003 | Ferrera et al. |
| 6,656,214 | B1 | 12/2003 | Fogarty et al. |
| 6,663,607 | B2 | 12/2003 | Slaikeu et al. |
| 6,679,903 | B2 | 1/2004 | Kurz |
| 6,743,236 | B2 | 6/2004 | Barry et al. |
| 6,835,185 | B2 | 12/2004 | Ramzipoor et al. |
| 6,852,261 | B2 | 2/2005 | Benjamin |
| 6,964,657 | B2 | 11/2005 | Cragg et al. |
| 6,997,937 | B2 | 2/2006 | Jacobsen et al. |
| 7,066,904 | B2 | 6/2006 | Rosenthal et al. |
| 7,070,608 | B2 | 7/2006 | Kurz et al. |
| 7,147,618 | B2 | 12/2006 | Kurz |
| 7,179,276 | B2 | 2/2007 | Barry et al. |
| 7,182,774 | B2 | 2/2007 | Barry et al. |
| 7,255,707 | B2 | 8/2007 | Ramzipoor et al. |
| 7,316,701 | B2 | 1/2008 | Ferrera et al. |
| 7,326,225 | B2 | 2/2008 | Ferrera et al. |
| 7,976,527 | B2 | 7/2011 | Cragg et al. |
| 8,454,649 | B2 | 6/2013 | Cragg et al. |
| 2003/0040733 | A1 | 2/2003 | Cragg et al. |
| 2003/0225365 | A1 | 12/2003 | Greff et al. |
| 2004/0260333 | A1 | 12/2004 | Dubrul et al. |
| 2010/0049165 | A1 | 2/2010 | Sutherland et al. |

FOREIGN PATENT DOCUMENTS

| | | |
|---|---|---|
| DE | 08614013 U1 | 8/1986 |
| DE | 3632573 C1 | 4/1988 |
| DE | 08619671 U1 | 4/1989 |
| DE | 19610333 | 9/1997 |
| DE | 29908453 U1 | 5/1999 |
| EP | 0375775 | 7/1990 |
| EP | 0446804 A2 | 3/1991 |
| EP | 0645161 B1 | 9/1994 |
| EP | 0747014 A1 | 12/1996 |
| EP | 1207791 B1 | 10/2004 |
| JP | 03168156 | 7/1991 |
| JP | 04-47416 | 4/1992 |
| JP | 07-508909 A | 10/1995 |
| NL | C 1008178 | 8/1999 |
| SU | 889009 | 12/1981 |
| WO | WO 91/12847 | 9/1991 |
| WO | 9316650 A1 | 9/1993 |
| WO | WO 93/17745 | 9/1993 |
| WO | WO 94/10936 | 5/1994 |
| WO | 9525480 A1 | 9/1995 |
| WO | 9618343 A1 | 6/1996 |
| WO | WO 97/27893 | 8/1997 |
| WO | 9745131 A1 | 12/1997 |
| WO | WO 99/22651 | 5/1999 |
| WO | WO 99/39649 | 8/1999 |
| WO | WO 99/42038 | 8/1999 |
| WO | WO 99/48548 | 9/1999 |
| WO | WO 00/01308 | 1/2000 |
| WO | WO 01/15608 | 3/2001 |

OTHER PUBLICATIONS

International Search Report for International Application No. PCT/US2009/054353, dated Dec. 30, 2009, in 13 pages.
Jeffree et al., The Porous, Guidewire-Directed, Detachable Aneurysms, American Society of Neuroradiology, 1999, Issue 774-779.
Kassell, et al., Size of Intracranial Aneurysms, Neurosurgery, 1983, vol. 12, Issue 3, pp. 291-297.
Office Action for Japanese Application No. 2001-519825, dated Jun. 8, 2009, in 14 pages.
Office Action for Japanese Application No. 2001-519825 dated May 21, 2010.
Schievink, Intracranial Aneurysms, The New England Journal of Medicine, 1997, pp. 28-40.
Szikora et al., Combined Use of Stents and Coils to Treat Experimental Wide-Necked Carotid Aneurysms: Preliminary Results, American Journal of Neuroradiology, 1994, vol. 15, pp. 1091-1102.
Szikora, et al., Endovascular Treatment of Experimental Aneurysms with Liquid Polymer: The Protective Potential of Stents, Neurosurgery, 1996, vol. 38, Issue 2, pp. 339-347.
Turjman, et al., Combined Stent Implantation and Endosaccular Coil Placement for Treatment of Experimental Wide-Necked Aneurysms: A Feasibility Study in Swine, American Journal of Neuroradiology, 1994, vol. 15, pp. 1087-1090.
Yoshimoto, et al., Cerebral Aneurysms Unrelated to Arterial Bifurcations, Acta Neurochirurgica 1996, vol. 138, pp. 958-964.
Sadato et al., "Immediately Detachable Coil for Aneurysm Treatment," AJNR Am J Neuroradiology, vol. 16, Aug. 1995, pp. 1459-1462.
Marks et al., "A Mechanically Detachable Coil for the Treatment of Aneurysms and Occlusion of Blood Vessels," AJNR Am J Neuroradiology, vol. 15, May 1994, pp. 821-827.
Reidy et al., "Interlocking Detachable Platinum Coils, A Controlled Embolization Device: Early Clinical Experience," vol. 19, No. 2, Mar. 1996, pp. 85-90.
Office Action from counterpart European Application No. 98961717, dated Sep. 10, 2002, 7 pp.
Partial Search Report from counterpart European Application No. 98961717, dated Oct. 10, 2000, 3 pp.
Response to Office Action dated Sep. 10, 2002, from counterpart European Application No. 98961717, filed Mar. 3, 2003, 27 pp.
Office Action from counterpart European Application No. 00965597.8, dated Jul. 8, 2002, 4 pp.
Response to Office Action dated Jul. 8, 2002, from counterpart European Application No. 00965597.8, filed Mar. 11, 2003, 7 pp.
International Search Report from International Application No. PCT/US1998/003344, dated Dec. 22, 1998, 1 pp.
International Preliminary Examination Report from International Application No. PCT/US00/40603, dated Jun. 13, 2002, 5 pp.
International Search Report from International Application No. PCT/US00/40603, dated Jan. 16, 2001, 4 pp.
Prosecution History from U.S. Appl. No. 10/242,469, dated Mar. 23, 2004 through Jul. 11, 2008, 93 pp.
Prosecution History from U.S. Pat. No. 6,964,657, dated May 27, 2003 through Jun. 15, 2005, 56 pp.
Prosecution History from U.S. Appl. No. 10/388,484, dated Mar. 17, 2003 through Mar. 23, 2006, 44 pp.
Prosecution History from U.S. Pat. No. 7,976,527, dated Oct. 24, 2007 through Mar. 9, 2011, 48 pp.
Prosecution History from U.S. Pat. No. 8,454,649, dated Aug. 1, 2012 through Jan. 30, 2013, 31 pp.
Notice of Reasons for Rejection, and translation thereof, from counterpart Japanese Application No. 2010-214921, dated May 2, 2012, 7 pp.
Notice of Reasons for Rejection, and translation thereof, from counterpart Japanese Application No. 2010-214921, dated Feb. 20, 2013, 7 pp.

* cited by examiner

DEVICE AND METHOD FOR CONTROLLING INJECTION OF LIQUID EMBOLIC COMPOSITION

CROSS-REFERENCE TO RELATED APPLICATIONS

This application is a continuation of U.S. patent application Ser. No. 13/152,208, filed Jun. 2, 2011, which is a continuation of U.S. patent application Ser. No. 11/923,495, filed Oct. 24, 2007, now U.S. Pat. No. 7,976,527, which is a continuation of U.S. patent application Ser. No. 10/242,469, filed Sep. 13, 2002, now abandoned, which is a continuation of U.S. patent application Ser. No. 09/387,274, filed Aug. 31, 1999, now U.S. Pat. No. 6,511,468, which is a continuation-in-part of U.S. patent application Ser. No. 08/953,149 filed Oct. 17, 1997, now U.S. Pat. No. 6,146,373, each of which is incorporated herein by reference in its entirety.

BACKGROUND OF THE INVENTION

1. Field of the Invention

The invention relates to a device for controlling injection of a liquid embolic composition into a patient, and more particularly, to a device for containment and restraint of a liquid embolic composition during and after solidification. The device for controlling injection may be incorporated in a catheter system used for delivery of the embolic composition in a controlled manner.

2. Description of the Related Art

In many clinical situations it is desirable to selectively occlude blood vessels for a variety of purposes, such as, the control or prevention of bleeding, the prevention of blood supply to tumors, treatment of arterial venous malformations (AVMs), and the blocking of blood flow within an aneurysm. Embolization of blood vessels has been performed by employing certain polymer compositions, particulates, and/or selerosing material including silicone balloons, metallic coils, PVA particles, gelatin, and the like, to selectively block blood flow in the blood vessels. However, these embolization procedures have certain drawbacks.

Intracranial aneurysms are abnormal blood filled dilations of a blood vessel wall which may rupture causing significant bleeding and damage to surrounding brain tissue or death. Traditionally, intracranial aneurysms have been surgically clipped to reduce the risk of rupture by placing a metal clip around the neck of the aneurysm to cut off and prevent further blood flow to the aneurysm. However, many aneurysms cannot be treated surgically because of either the location and configuration of the aneurysm or because the condition of the patient does not permit cranial surgery.

When aneurysms cannot be treated surgically or when surgery is considered to be too risky or invasive, aneurysms may be treated endovascularly with coils. The coils are placed in the aneurysm by extending a catheter endovascularly to the site of the aneurysm and passing single or often multiple metallic coils such as platinum, stainless steel, or tungsten coils through the catheter into the aneurysm. The coils placed within the aneurysm create a thrombus which occludes the aneurysm and prevents further blood flow to the aneurysm. The treatment of intracranial aneurysms with coils isolates the aneurysm from arterial circulation, helping to guard against rupture and further growth of the aneurysm. However, the use of metallic coils to treat intracranial aneurysms may not be a permanent solution because the blood clot around the coils may lyse or dissolve due to the dynamic nature of the blood clotting function. Once a clot formed around the coils in an aneurysm lyses, the coil can no longer perform its function of occluding the aneurysm. In addition, the coils may become dislodged, move from the aneurysm, and enter the patient's blood stream causing blockages at other locations within the vascular system. Coils can also form a loop extending into the blood stream which generates undesirable embolisms downstream.

Another drawback associated with the use of coils to occlude an aneurysm is that the coils are known to compact over time leaving cavities for subsequent aneurysm growth. In addition, if a subsequent surgical clipping procedure is warranted, it can be difficult to place the clip over the coil mass.

Other procedures for treating aneurysms include occluding the aneurysm with a silicone balloon or filling the aneurysm with particulate material.

Aneurysms having large necks are not easily treated by either surgical clipping or by coils because the aneurysm neck may have a shape which cannot be completely clipped surgically and the coils may tend to become dislodged from the aneurysm when the neck is particularly large.

One minimally invasive procedure for treating intracranial aneurysms which addresses the problems with the surgical clipping and coil techniques involves the endovascular injection of a liquid embolic composition which solidifies in the aneurysm to occlude the aneurysm. Typically, liquid embolic compositions include a water insoluble, biocompatible, non-biodegradable polymer, dissolved in a biocompatible solvent. Once the liquid embolic composition is injected into the aneurysm, the biocompatible solvent dissipates into the blood and the polymer solidifies to occlude the blood flow through the aneurysm. These liquid embolic compositions preferably include a radiopaque material which allows the physician to view the embolization procedure by fluoroscopy.

Prior to delivery of the liquid embolic composition to the aneurysm, the aneurysm and delivery device are preferably positioned so that the liquid embolic composition will be delivered by gravity into the aneurysm and will solidify and remain in the aneurysm. This means that the patient position is often manipulated to position the aneurysm with the aneurysm neck pointing up. As the embolic composition is delivered to the aneurysm, the solvent dissipates from the polymer material and is removed in the blood stream causing the polymer material within the aneurysm to solidify.

Depending on the rate at which the liquid embolic material is injected into the blood vessel and the amount' of blood flow present, the polymer may remain in liquid form for a period of time while the solvent dissipates into the blood stream. In addition, the solvent concentration at the point of injection may increase to a point where small strings of unsolidified polymer material may separate from the polymer mass and be carried away in the blood stream where the polymer can occlude an undesired vascular location.

Accordingly, it would be desirable to provide a device or method for controlling the solidification of the polymer material during injection so that an aneurysm which is in a non-gravity dependent position can be filled without causing the liquid embolic composition to pass out of the aneurysm into the blood stream. It would also be desirable to prevent polymer strings from being carried away in the blood stream.

SUMMARY OF THE INVENTION

The present invention relates to a containment member for trapping an injected liquid embolic composition to prevent the liquid embolic from solidifying outside of an embolization area.

In accordance with one aspect of the present invention, a liquid embolic delivery system includes a catheter having a lumen for delivery of a liquid embolic composition to a cavity, a containment member positioned at a distal end of the catheter, and a detachment mechanism for completely detaching the containment member from the catheter after solidification of the liquid embolic composition to allow separation of the catheter from a mass of solidified embolic composition. The containment member is shaped to trap the liquid embolic composition delivered through the lumen of the catheter.

In accordance with an additional aspect of the present invention, a method of containing a liquid embolic composition at an embolization site within a body includes the steps of delivering a liquid embolic composition to an embolization site within a body with a catheter, containing the liquid embolic composition during solidification with a containment member, and detaching the containment member from the catheter after solidification of the liquid embolic composition to release the catheter from a mass of solidified embolic composition.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF THE PREFERRED EMBODIMENTS

The liquid embolic delivery system includes a catheter having a lumen through which liquid embolic composition is delivered to an embolization site within the body. A containment member, such a nidus or a flexible sack is positioned at the distal end of the catheter and, the liquid embolic composition is injected into the containment member. The liquid embolic composition is trapped or meshes with the containment member during solidification containing the liquid embolic and preventing the liquid embolic composition from passing into the blood stream. The preferred embodiments of the containment member for use with the delivery system will be discussed below with respect to the various figures.

Prior to discussing the present invention in further detail, the following terms are defined:

The term "liquid embolic composition" refers to a fluid composition that is injected at an embolization site and solidifies to fully or partially occlude the embolization site.

The term "embolizing" or "embolization" refers to a process wherein a fluid composition is injected into a blood vessel or tissue which, in the case of, for example, aneurysms fills or plugs the aneurysm sack and/or encourages clot formation so that blood flow into the aneurysm and pressure in the aneurysm ceases, and in the case of arterial venous malformations (AVMs) and arterial venous fistula (AVFs) forms a plug or clot to control/reroute blood flow to permit proper tissue perfusion. Embolization may be used for preventing or controlling bleeding due to lesions (e.g., organ bleeding, gastrointestinal bleeding, vascular bleeding, as well as bleeding associated with an aneurysm). In addition, embolization can be used to ablate diseased tissue (e.g., tumors, etc.) by cutting off the blood supply.

The liquid embolic composition for use in the present invention may be any biocompatible composition which solidifies within the body, for example a biocompatible polymer combined with a suitable biocompatible solvent such as ethanol, dimethylsulfoxide (DMSO), ethyl lactate, acetone, and the like. Examples of embolizing compositions are described in U.S. Pat. No. 5,667,767, which issued Sep. 16, 1997, U.S. Pat. No. 5,580,568, which issued Dec. 3, 1996, and U.S. patent application Ser. No. 08/688,050 each of which are incorporated herein by reference in their entirety.

According to one preferred embodiment of the invention in which the solvent used is DMSO, the delivery system elements which may come into contact with the solvent are DMSO compatible. Examples of DMSO compatible catheter materials include polyolefins, such as polyethylene or polypropylene; fluoropolymers, such as PTFE and ETFE, and silicones.

Figure 1:
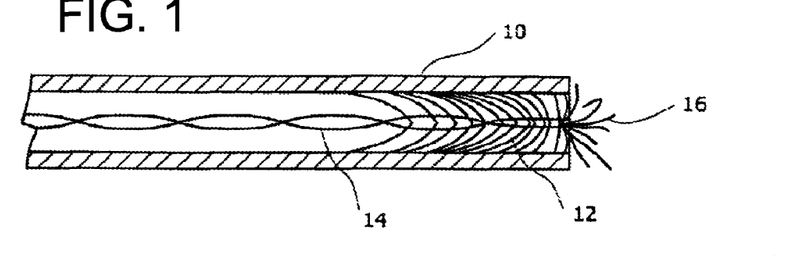
FIG. 1 is a side cross sectional view of a first embodiment of a liquid embolic delivery system with a multifilament brush in a retracted position.
Figure 2:
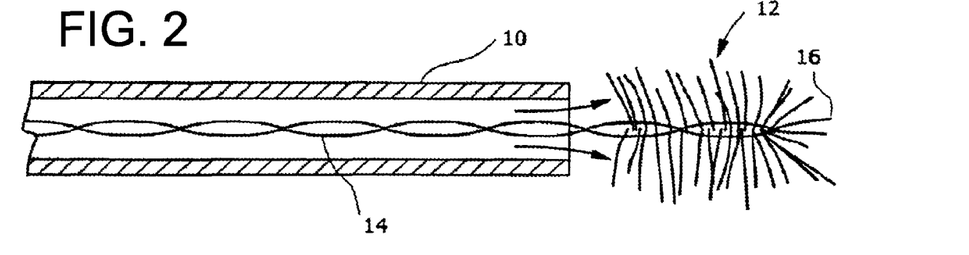
FIG. 2 is a side cross sectional view of the delivery system of FIG. 1 with the multifilament brush in the extended position.

The liquid embolic delivery system as shown in FIGS. 1 and 2 includes an elongated flexible catheter 10 and a containment brush 12 disposed within the catheter. The catheter 10 may be an over the wire catheter, a flow directed catheter, or any other type of catheter capable of delivering the liquid embolic composition to the embolization site. The brush 12 includes an elongated flexible shaft 14 which extends through the lumen of the catheter 10 for manipulation of the brush from the proximal end of the catheter which extends outside the patient's body. The brush 12 includes a plurality of filaments 16 extending substantially radially from a distal end of the shaft 14.

In use, the catheter 10 is delivered to an embolization site with the brush 12 in the refracted position, shown in FIG. 1, in which the brush is positioned fully or substantially within the lumen. The shaft 14 is then moved distally within the catheter 10 to extend the brush 12 from the distal end of the catheter. The brush 12 is positioned such that the liquid embolic composition exiting the lumen of the catheter 10 will become trapped by the brush. Preferably, the brush is positioned about 0 to 5 mm, more preferably about 1 to 4 mm from the distal end of the catheter with the exact position depending on the particular embolization site and procedure being performed.

Once the brush 12 has been positioned the liquid embolic composition is then injected through the catheter 10 either through the same lumen in which the shaft 14 of the brush 12 extends or through a second parallel lumen of the catheter. As the liquid embolic composition is delivered down the catheter the liquid which exits the distal end of the catheter is injected into the filaments 16 of the brush 12. The solvent begins to dissipate from the liquid embolic composition and the polymer material precipitates and meshes with the bristles of the brush. Subsequent injections of liquid embolic material increase the mass of solidified embolic material surrounding the brush at the embolization site. Injection of the liquid embolic composition continues until the embolization site is completely embolized. The brush 12 acts to contain and trap the precipitating material and prevent the effects of gravity and blood flow from causing the polymer material to be carried away from the embolization site.

After the liquid embolic composition has been delivered through the catheter 10 and has formed a solid mass around the brush 12, the mass is detached from the catheter and the brush shaft 14 by a detachment mechanism, such as a mechanical, electrical, or chemical detachment system as discussed below.

Figure 2A:
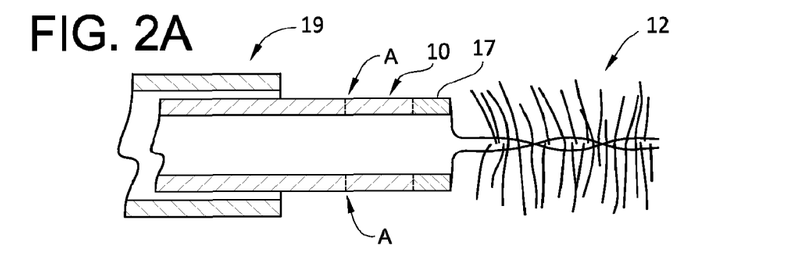
FIG. 2A is a side cross sectional view of a second embodiment of a liquid embolic delivery system, in which the entire distal end of the catheter is detachable.

With reference to FIG. 2A, although the brush 12 has been described as attached to an elongated flexible shaft 14 which extends through the lumen of the catheter 10, the brush may also be connected by a mounting member 17, such as a short shaft, directly to the distal end of the catheter. When the brush 12 is connected directly to the end of the catheter 10 the catheter and brush may be introduced together as a single unit through a separate introducing catheter 19 of a larger diameter than the catheter 10. After delivery of liquid embolic composition the brush 12 may be detached from the catheter 10 or the entire distal end of the catheter may be detachable (as indicated by the dashed lines and arrows "A" in FIG. 2A).

The filaments 16 of the brush 12 are preferably flexible members formed of a material such as nylon, polyethylene, polypropylene, polyester, PTFE, Dacron, and the like. The filaments are preferably soft, flexible, absorbent, biocompatible, and DMSO compatible. The filament size may vary depending on the application, however, one example of a suitable filament has a diameter of about 75 to about 500 microns, preferably about 150 to about 250 microns, and a length depending on an inner diameter of the vascular site of about 1 to about 30 mm, preferably about 2 to about 10 mm.

Figure 3:
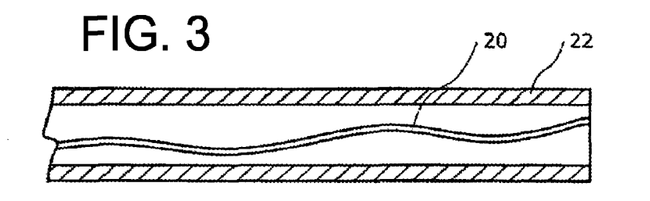
FIG. 3 is a side cross sectional view of a delivery system according to a third embodiment prior to formation of a nest.
Figure 4:
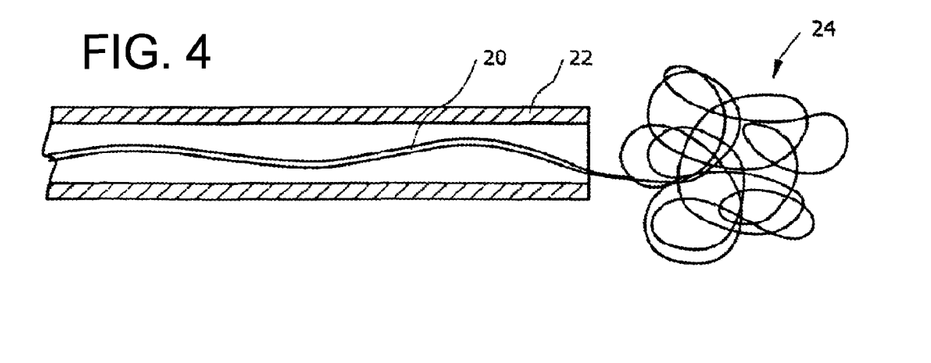
FIG. 4 is a side cross sectional view of the delivery system of FIG. 3 with a nest formed.

FIGS. 3 and 4 illustrate an alternative embodiment of the liquid embolic delivery system in which a wire 20 is delivered through the lumen of a catheter 22 when the wire 20 exits the distal end of the catheter 22 the wire forms into a nest configuration at the embolization site. The wire 20 is preformed with a curvature which creates the nest 24 when the wire is delivered out of the distal end of the catheter 22. The shape of the nest 24 generally conforms to the shape of the embolization site, for example, when treating an aneurysm the nest 24 will conform to the shape of the aneurysm. The liquid embolic composition is subsequently delivered through the catheter lumen and is trapped by and precipitates on the wire nest 24. As in the embodiment described above, after embolization is complete, the solidified mass of embolic material and the wire nest 24 are detached from the catheter.

The wire 20 may be preformed to cause the nest 24 to take on a particular predetermined shape. Examples of nest shapes include the randomly curving wire shape shown in FIG. 4 and a coil or spiral shape. The wire 20 may be formed of a biocompatible material, such as, stainless steel, platinum, Nitinol, gold, tungsten, and the like. In addition, it may be desirable to form the wire 20 from a shape memory material, such as Nitinol.

Figure 5:
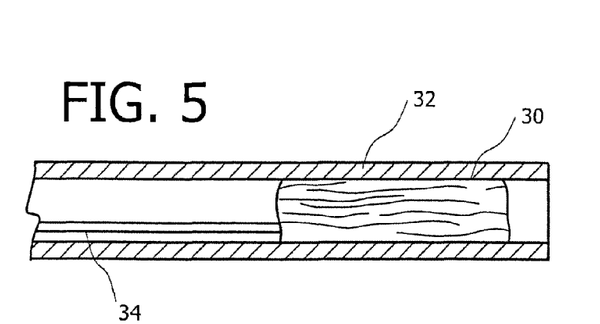
FIG. 5 is a side cross sectional view of a delivery system according to a fourth embodiment with a sponge in a retracted position.
Figure 6:
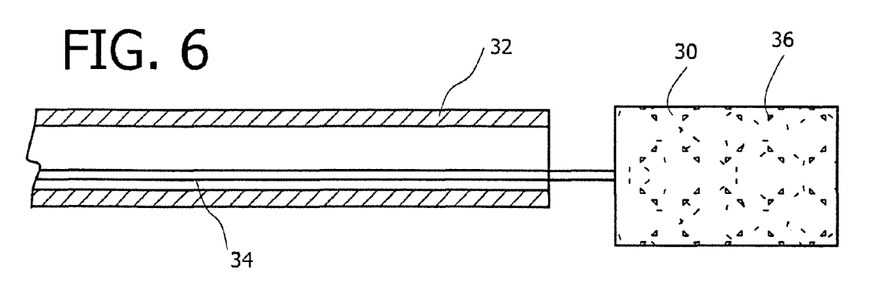
FIG. 6 is a side cross sectional view of the delivery system of FIG. 5 with the sponge in the extended position.

Another alternative embodiment of the invention including a sponge like member 30 and a catheter 32 is illustrated in FIGS. 5 and 6. As shown in FIG. 5, the sponge 30 is compressed within the lumen of the catheter 32 during delivery of the catheter to the embolization site. Once the distal tip of the catheter 32 is located at or near the embolization site, the sponge 30 is deployed from the catheter by a plunger or rod 34 which extends through the catheter lumen 32 and connects to the sponge 30. Once the sponge 30 has been deployed from the catheter 32 the sponge expands to the configuration shown in FIG. 6. The expanded sponge 30 includes a plurality of large holes 36 and smaller pores into which the liquid embolic composition is injected.

As in the embodiment of FIGS. 1 and 2, the sponge 30 of FIGS. 5 and 6 may be fixed to the end of the catheter 32 instead of to the plunger 34 and the entire catheter and sponge system may be delivered to the embolization site through an introducing catheter. The liquid embolic composition may then be delivered by the catheter 32 to an exterior or an interior of the sponge. Once an embolic mass has formed around the sponge 30 by injection of the liquid embolic composition through the catheter lumen, the embolic mass is detached from the catheter 32 and remains within the embolization site after the catheter has been removed. The detachment of the solidified embolic mass from the catheter 32 and the rod 34 is performed by mechanical, electrical, or chemical detachment as will be described further below.

The sponge member 30 according to the embodiment of FIGS. 5 and 6 is formed of a biocompatible, open cell, compressible material having a high porosity, such as polyethylene sponge, polypropylene sponge, polyurethane sponge, PVA, fluoropolymer, and the like. The size and shape of the sponge 30 will be modified to properly fit within the particular embolization site. The sponge material is preferably a biocompatible, DMSO compatible, non-toxic, soft, hydrophilic material which fully fills the aneurysm. An expansion ratio of the sponge is preferably about 5:1 to 20:1, more preferably about 10:1.

Figure 7:
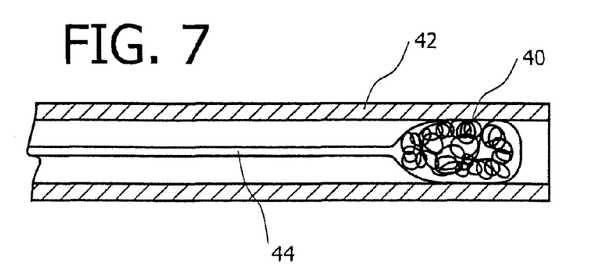
FIG. 7 is a side cross sectional view of a delivery system according to a fifth embodiment with a swab in a retracted position.
Figure 8:
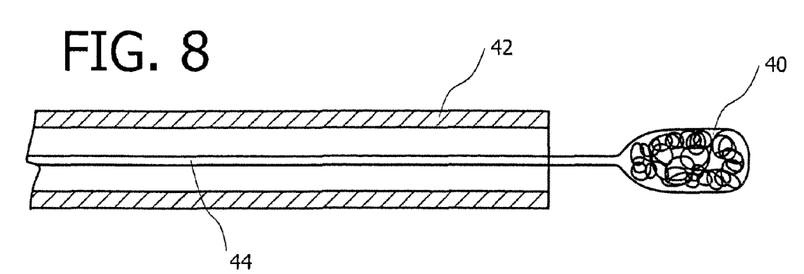
FIG. 8 is a side cross sectional view of the delivery system of FIG. 7 with the swab in the extended position.

FIGS. 7 and 8 relate to a further alternative embodiment of the invention in which the containment member for trapping the liquid embolic composition is a swab shaped member 40 of a filamentous material. The swab shaped member 40 may be compressed within and deployed from the lumen of a catheter 42 by a pusher or rod 44 or can be permanently affixed to the distal end of the catheter and inserted through an introducing catheter. The liquid embolic composition which is delivered through the catheter 42 is trapped in and around the swab shaped member 40. Additional embolic composition solidifies in shells around the core provided by the swab shaped member 40. Appropriate materials for the swab shaped member 40 include biocompatible materials, such as polyester, PTFE, silk, Dacron, polyethylene, nylon, fluoropolymer, cotton, and the like. The shape and size of the swab 40 may be modified to correspond with a particular shape and size of an embolization site.

Figure 9:
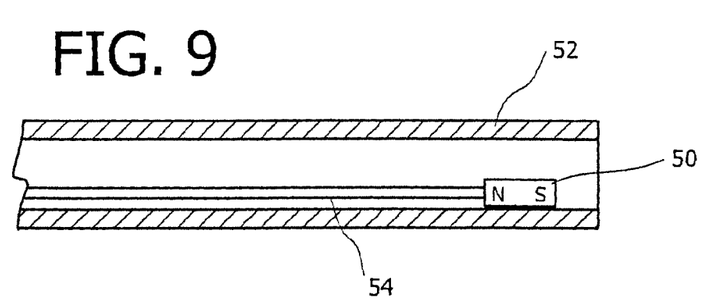
FIG. 9 is a side cross sectional view of a delivery system according to a sixth embodiment with a magnetic member in a retracted position.
Figure 10:
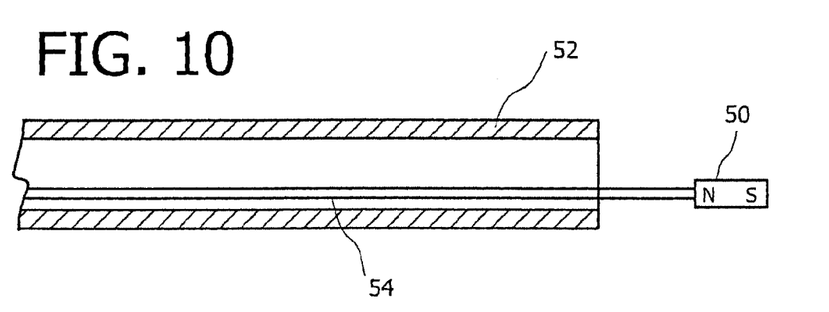
FIG. 10 is a side cross sectional view of the delivery system of FIG. 9 with the magnetic member in the extended position.

A further embodiment of the liquid embolic delivery system, as shown in FIGS. 9 and 10, includes a node 50, such as an electrically charged member or a magnet, which attracts the liquid embolic composition delivered through the lumen of a catheter 52. The node 50 can be fixed on the end of the catheter 52 or preferably is movable from a refracted position, shown in FIG. 9, to an extended position, shown in FIG. 10, by a rod 54 extending through the catheter lumen. The polymer preferably includes magnetic particles, which are attracted to the node. The node 50 is positioned generally in a center of an embolization site and the liquid embolic agent solidifies in shells around the node.

Figures 11, 12, 13:
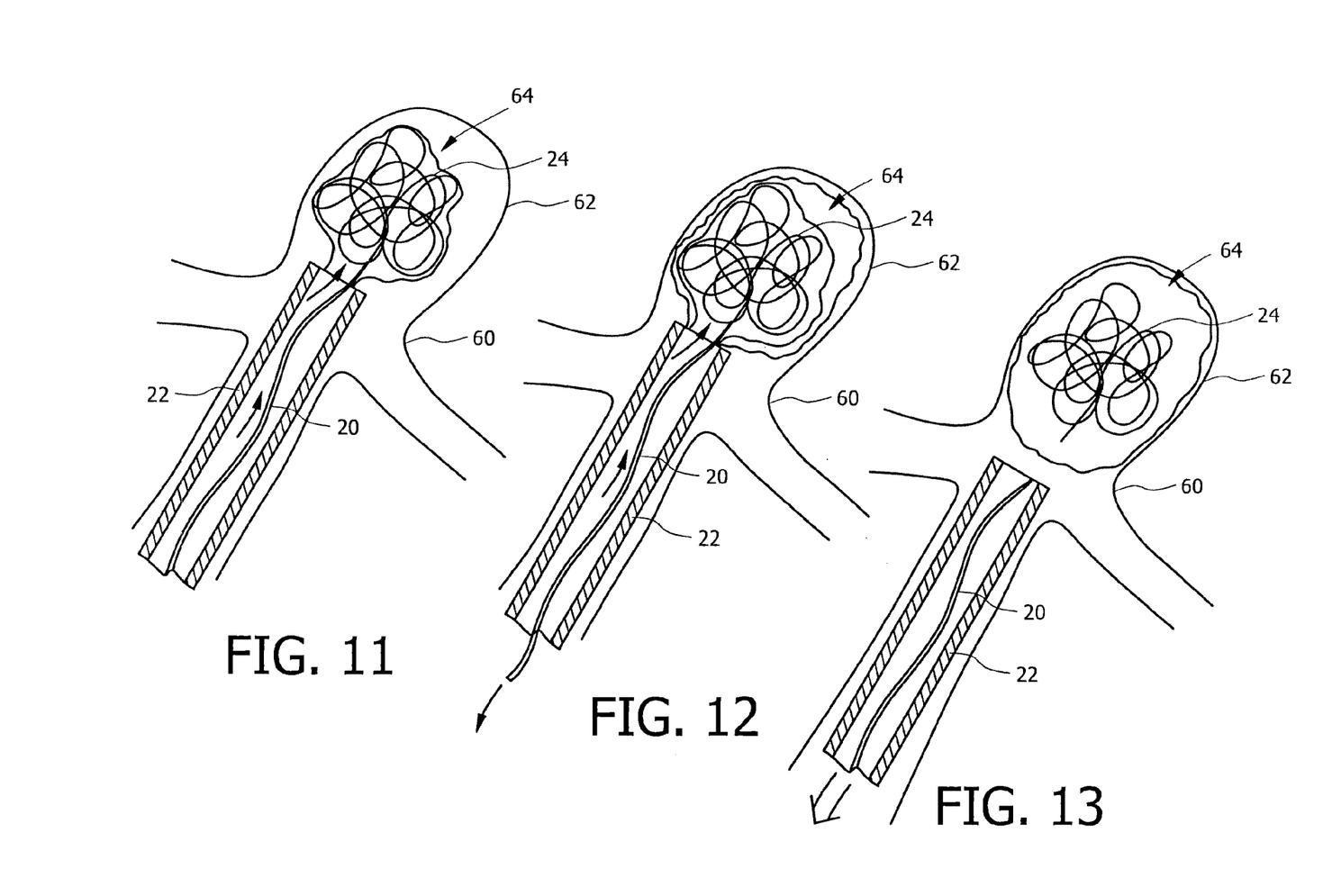
FIG. 11 is a side cross sectional view of an aneurysm being treated by the delivery system of FIGS. 3 and 4.
FIG. 12 is a side cross sectional view of an aneurysm with a mass of liquid embolic material filling the aneurysm.
FIG. 13 is a side cross sectional view of an aneurysm after the delivery system has been detached from the mass of liquid embolic material.

FIGS. 11-13 illustrate a method of treating an aneurysm with the liquid embolic delivery system having the wire nest 54 which has been described above with respect to FIGS. 3 and 4. As shown in FIG. 11, the catheter 22 is positioned at or near a neck 60 of an aneurysm 62 and the wire 20 is passed through the lumen of the catheter 22 to form a wire .nest 24 within the aneurysm. The liquid embolic material is then injected through the lumen of the catheter 22 and is trapped by the wire nest 24 during solidification. Injection of the liquid embolic material continues until the aneurysm 62 is completely or substantially filled with an embolic mass 64 as illustrated in FIG. 12. The catheter is then detached from the solidified mass 64 of liquid embolic material within the aneurysm by chemical, mechanical, or electrical detachment means. For example, the mass 64 of embolic composition may be detached by holding the catheter 22 stationary while pulling the wire 20 proximally within the catheter lumen to break the wire at a location where the wire enters the liquid embolic mass. The catheter 22 and the wire 20 are then removed from the embolization site leaving the liquid embolic mass 64 and the wire nest 24 embedded within the mass in the aneurysm. The wire 20 which has been broken as described above may also be used as a pusher to separate the embolic mass 64 from the catheter 22. This method of treating an aneurysm may also be used for other embolization treatments.

The liquid embolic delivery system according to the present invention may be configured so that injection of liquid embolic composition forms as consecutive shells over a beginning kernel as the embolic mass increases in size.

Alternatively, the liquid embolic may be injected from a center of the containment member so that an outer skin is created first and additional embolic is added inside the mass causing the outer skin to expand.

Figure 14:
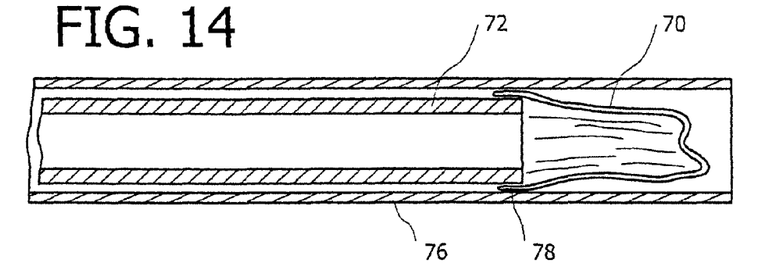
FIG. 14 is a side cross sectional view of a delivery system according to a seventh embodiment including a flexible sack in a retracted position.
Figure 15:
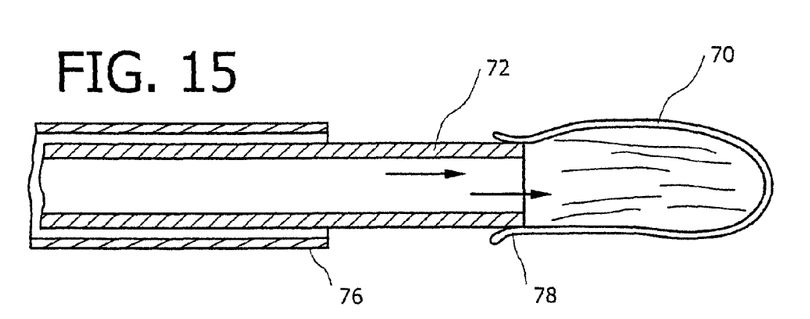
FIG. 15 is a side cross sectional view of the delivery system of FIG. 14 with the flexible sack in the extended position.
Figure 16:
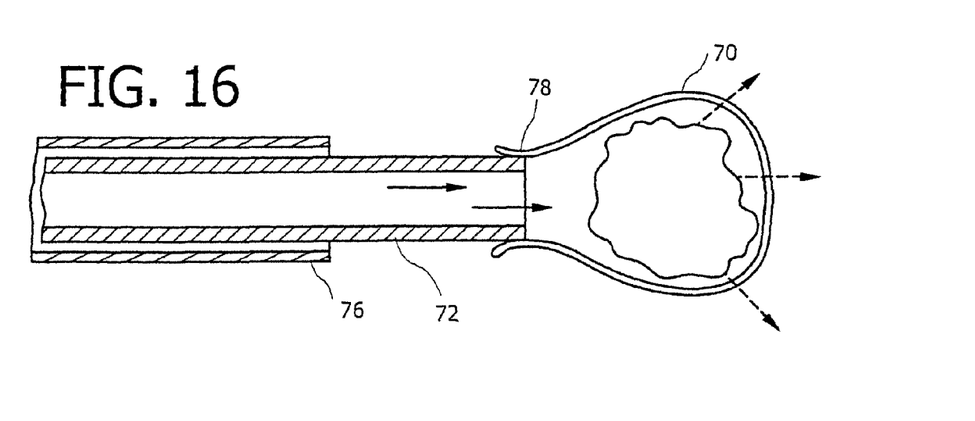
FIG. 16 is a side cross sectional view of the delivery system of FIG. 14 in which liquid embolic composition has solidified within the flexible sack.

FIGS. 14-16 illustrate a liquid embolic delivery system including a flexible sack 70 affixed to a distal end of a catheter 72. The edges 78 of the flexible sack 70 are affixed in a known manner to an exterior of the catheter distal tip such that the flexible sack surrounds the catheter outlet. The catheter 72 having the flexible sack 70 affixed to the distal end are delivered to an embolization site through an introducer catheter 76 having a somewhat larger diameter than the catheter 72. Once the flexible sack 70 is placed within the embolization site such as within an aneurysm, a liquid embolic composition is injected through the catheter lumen.

The flexible sack 70 is formed of a membrane or woven material which is substantially impermeable to the precipitate of the liquid embolic composition while being permeable to the solvent to allow the solvent to dissipate from the liquid embolic material injected into the flexible sack. Examples of biocompatible materials which may be used to form the flexible sack 70 include polyester, PTFE, urethane, Dacron, nylon, polyethylene, fluoropolymers, silicone, and the like. According to one embodiment, the flexible sack is a mesh bag having a structure which allows the diameter of the bag to increase as the embolic composition is injected. The mesh material may be non-elastic or may be elastic acting like a balloon. The mesh allows the solvent to dissipate out of the bag while the structure of the bag prevents fingers or strands of embolic material from passing out of the embolization area. The flexible sack 70 is detachable from the distal end of the catheter 72 once the embolization is complete so that the catheter can be removed from the embolization site.

The method of detachment of any one of the containment members described above from the catheter of the present invention may be either mechanical, electrical, or chemical. One example of a mechanical method of detachment involves forcibly detaching the mass of embolic material and the containment member from the distal tip of the catheter such as by use of a plunger member extending through the lumen of the catheter. Alternatively, an outer catheter sleeve may be used to strip a mass from a distal tip of the catheter. Mechanical detachment can also be performed by various interlocking, pushing, twisting, and locking motions.

Electrical detachment may be performed by providing a weakened section at a junction between the containment member and the catheter which is easily vaporized by application an electric current. For example, a 9V electric power source may apply a current of about 0.3 mA for detachment. One example of an electrical detachment mechanism is described in U.S. Pat. No. 5,928,226, which is incorporated herein by reference.

Finally, with a chemical detachment mechanism, a dissolvable detachment section is included in the delivery system between the catheter and the containment member or at the distal end of the catheter. The dissolvable detachment section is dissolved, softened, swollen, degraded, or otherwise changed by the injection of a biocompatible chemical through the catheter. Some examples of chemical detachment systems include dissolvable detachment sections, such as a polymer section which is dissolved by DMSO, a nylon section which is dissolved by a fluorinated hydrocarbon, or sections which are dissolved by saline or any of the other biocompatible solvents discussed above.

FIGS. 17-20 illustrate a liquid embolic delivery system which disturbs the blood flow into and out of the aneurysm to improve control over injection of the liquid embolic composition. The disturbance of blood flow into and out of the aneurysm through the aneurysm neck creates a low turbulence or "peaceful" fluid environment within the aneurysm which allows improved filling of the aneurysm with the embolic material.

Figure 17:
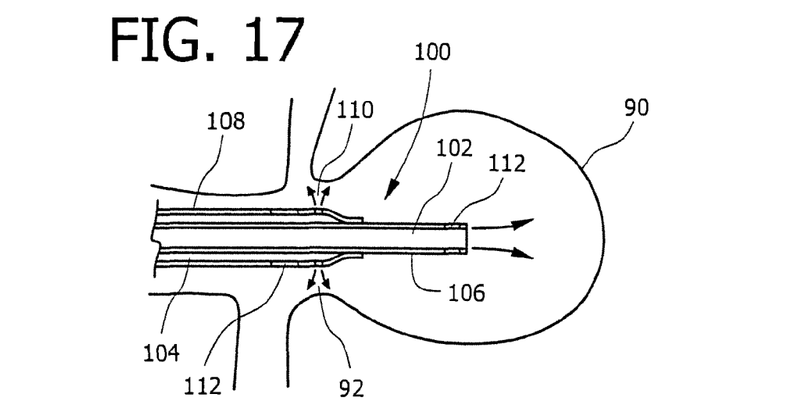
FIG. 17 is a side cross sectional view of an aneurysm with an aneurysm neck flow disruption system.

As shown on FIG. 17, a delivery system 100 is placed at an embolization site such as an aneurysm 90 having an aneurysm neck 92. The delivery system has two lumens including an inner lumen 102 for delivery of the liquid embolic composition and an outer lumen 104 for injection of a fluid such as saline which is used to disrupt blood flow at the aneurysm neck 92. The delivery system 100 may be formed from an inner catheter 106 and an outer catheter 108 concentrically surrounding the inner catheter and having a plurality of side ports 110 which can be positioned at the aneurysm neck 92. A distal end of the outer catheter 108 forms a fluid tight seal with an exterior of the inner catheter 106. This distal end of the outer catheter 108 may be permanently bonded to the inner catheter or may be slideable over the inner catheter with or without a valve member. The inner and outer catheters 106, 108 may be provided with radiopaque markers 112 for visualization of the position of the inner and outer catheters. Alternatively, a radiopaque marker may be sandwiched between the two tubes at a fuse joint at the distal end of the outer catheter 108.

The side holes 110 are preferably spaced around the outer catheter 108 and are positioned within an area of a relatively short axial length. In use, the delivery system 100 is guided to an aneurysm over a guidewire using the inner catheter lumen 102 as a guidewire lumen. The tip of the inner lumen is located within the dome of the aneurysm and the side holes 110 are positioned near the aneurysm neck 92. The guidewire is then removed and the disruption fluid is then injected through the outer catheter 108 and exits the side holes 110 of the delivery device. The disruption fluid can be any biocompatible fluid such as saline, contrast medium, or mixtures thereof. The flow of the disruption fluid is visualized and adjusted so that optimum disruption of blood flow at the aneurysm neck occurs. The liquid embolic material is then injected through the lumen 102 of the center catheter 106 until the aneurysm 90 has been filled and the embolic composition is solidified.

According to one embodiment of the present invention, the inner catheter 106 is slideable with respect to the outer catheter 108 to allow adjustment of the distance between the distal tip where the liquid embolic composition is injected and the disruption side holes 110. The ability to adjust the delivery device 100 in this manner is useful because aneurysm vary in size. A valve at the distal end of the outer catheter 108 can allow the outer catheter to slide easily over the inner catheter in an axial direction without the leakage of fluid.

Figure 18:
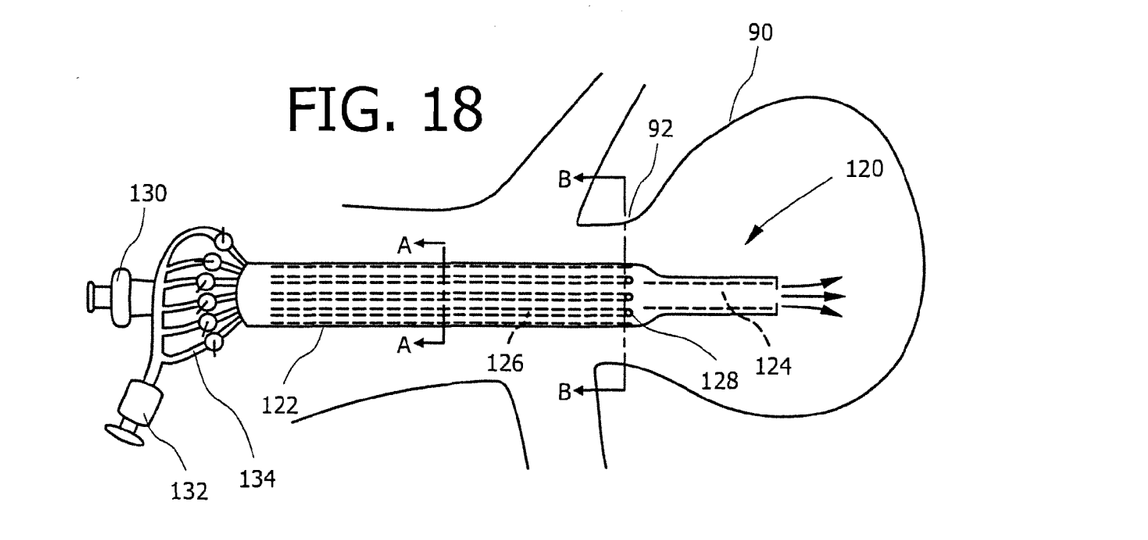
FIG. 18 is a side cross sectional view of an aneurysm with an alternative embodiment of an aneurysm neck flow disruption system.
Figure 19:
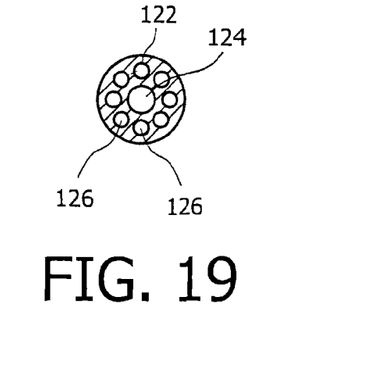
FIG. 19 is a cross sectional view taken along line A-A of FIG. 18.
Figure 20:
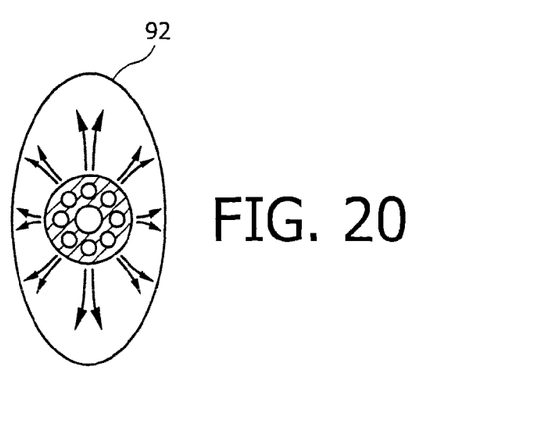
FIG. 20 is a cross sectional view taken along line B-B of FIG. 18.

FIGS. 18-20 illustrate an alternative embodiment of a delivery system 120 which allows a pattern of the disruption flow to be controlled. Because the necks 92 of many aneurysms 90 have non-circular or elliptical cross sections, it may be desirable to vary the flow rate of the aneurysm neck disrupting fluid out of different side holes around the circumference of the delivery system. In other words, it may be desirable to increase the disruption fluid flow at side holes which are oriented in a direction of a major axis of the elliptical neck while decreasing the flow at side holes which are oriented in the direction of the minor axis of the elliptical neck.

FIG. 18 illustrates an aneurysm 90 having an elliptical aneurysm neck 92 and a delivery system 120 for delivery of liquid embolic composition and disruption fluid to the aneurysm. The delivery system 120 includes an elongated catheter 122 with a central lumen 124 and a plurality of surrounding lumens 126. The surrounding lumens 126 are spaced around the central lumen 124 and each include a side port 128 for delivery of the disruption fluid. FIG. 19 shows a cross section of the catheter 122 taken along line A-A illustrating the central lumen 124 and a plurality of surrounding lumens 126.

At a proximal end of the catheter 122 a fluid connection 130 is provided for connection of the central lumen to a source of the liquid embolic composition. A fluid connection 132 is also provided for connection of the plurality of surrounding lumens 126 to a source of disruption fluid. A manifold 134 and a plurality of valves are provided for controlling delivery of the disruption to the different surrounding lumens 126 at relatively variable velocities. The manifold 134 and valves provide a flow regulating means for delivery of the fluid which allows the fluid delivered from the different side ports 128 at the aneurysm neck 92 to be carefully controlled as illustrated in FIG. 20.

According to a further embodiment of the liquid delivery having aneurysm neck disruption side flow; one or more rows of side holes may be provided. These rows of side holes may be positioned just inside and just outside the aneurysm neck to further disrupt the blood flow through the neck.

While the invention has been described in detail with reference to the preferred embodiments thereof, it will be apparent to one skilled in the art that various changes and modifications can be made and equivalents employed, without departing from the present invention.

What is claimed is:

1. A system comprising:
   an inner catheter defining an inner catheter lumen;
   an outer catheter defining an outer catheter lumen and a plurality of side ports, wherein the outer catheter surrounds the inner catheter, a distal end of the outer catheter forming a fluid tight seal with an exterior surface of the inner catheter when a distal end of the inner catheter extends past the distal end of the outer catheter, wherein the inner catheter is slideable with respect to the outer catheter to adjust a distance between the distal end of the inner catheter and the side ports;
   a liquid embolic composition source fluidically connected to the inner catheter lumen; and
   a disruption fluid source fluidically connected to the outer catheter lumen, the disruption fluid comprising saline, a contrast medium, or a mixture of saline and the contrast medium.

2. The system of claim 1, wherein the inner catheter and the outer catheter each comprises a radiopaque marker.

3. The system of claim 1, further comprising a radiopaque marker between the inner catheter and the outer catheter.

4. The system of claim 1, further comprising a valve at the distal end of the outer catheter, wherein the valve is configured to allow the outer catheter to slide over the inner catheter in an axial direction without the leakage of fluid from the outer catheter lumen.

5. The system of claim 1, wherein the outer catheter defines one row of side ports.

6. The system of claim 1, wherein the outer catheter defines a plurality of rows of side ports, each row of side ports being axially spaced from an adjacent row of side ports.

7. The system of claim 1,
   wherein the disruption fluid comprises the saline.

8. The system of claim 1, further comprising:
   a liquid embolic composition disposed within the inner catheter lumen; and
   a disruption fluid disposed within the outer catheter lumen.

9. The system of claim 1, further comprising:
   a liquid embolic composition disposed within the inner catheter lumen; and
   saline disposed within the outer catheter lumen.

10. The system of claim 1, wherein the disruption fluid comprises the contrast medium.

11. The system of claim 1, wherein the disruption fluid comprises the mixture of saline and the contrast medium.

12. A method comprising:
   guiding a delivery system to a target location within a patient, the delivery system comprising:
      an inner catheter defining an inner catheter lumen; and
      an outer catheter defining an outer catheter lumen and a plurality of side holes, wherein the outer catheter surrounds the inner catheter, a distal end of the outer catheter forming a fluid tight seal with an exterior surface of the inner catheter, wherein the inner catheter is slideable with respect to the outer catheter to adjust a distance between a distal tip of the inner catheter and the side ports;

delivering a disruption fluid via the outer catheter lumen and the side holes defined by the outer catheter, the disruption fluid comprising saline, a contrast medium, or a mixture of saline and the contrast medium; and delivering a liquid embolic material via the inner catheter lumen.

13. The method of claim 12, wherein guiding the delivery system to the target location comprises positioning a distal end of the inner catheter within a dome of an aneurysm.

14. The method of claim 12, wherein guiding the delivery system to the target location comprises positioning the side holes defined by the outer catheter inside and outside a neck of an aneurysm.

15. The method of claim 12, wherein guiding the delivery system to the target location comprises sliding the inner catheter with respect to the outer catheter to adjust a distance between a distal tip of the inner catheter and the side holes.

16. The method of claim 12, wherein the disruption fluid comprises the saline.

17. The method of claim 12, wherein the disruption fluid comprises the contrast medium.

18. The method of claim 12, wherein the disruption fluid comprises the mixture of saline and the contrast medium.

* * * * *